US00PP18770P2

(12) United States Plant Patent
Carruth

(10) Patent No.: US PP18,770 P2
(45) Date of Patent: Apr. 29, 2008

(54) HYBRID TEA ROSE PLANT NAMED 'WEKVOOSUN'

(50) Latin Name: *Rosa hybrida*
Varietal Denomination: WEKvoosun

(75) Inventor: Thomas F. Carruth, Altadena, CA (US)

(73) Assignee: Weeks Wholesale Rose Grower, Inc, Pomona, CA (US)

( * ) Notice: Subject to any disclaimer, the term of this patent is extended or adjusted under 35 U.S.C. 154(b) by 0 days.

(21) Appl. No.: 11/606,699

(22) Filed: Nov. 30, 2006

(51) Int. Cl.
*A01H 5/00* (2006.01)

(52) U.S. Cl. ..... Plt./132

(58) Field of Classification Search ..... Plt./130, Plt./131, 132, 136, 138, 139
See application file for complete search history.

*Primary Examiner*—Howard J. Locker

(57) ABSTRACT

A new variety of Hybrid Tea rose suitable for garden decoration, having flowers of blended orange and pink coloration.

1 Drawing Sheet

Classification: The present invention relates to a new *Rosa hybrida* plant.

Variety Denomination: The new plant has the varietal denomination 'WEKvoosun'.

BACKGROUND OF THE INVENTION

This invention relates to a new and distinct variety of Hybrid Tea Rose. It has as its seed parent the variety known as 'AROmiclea' (U.S. Plant Pat. No. 6,121) and as its pollen parent the variety known as 'FRYxotic' (U.S. Plant Pat. No. 9,718).

SUMMARY OF THE INVENTION

Among the features which distinguish the new variety from other presently available and commercial rose cultivars known to the inventor are the following combination of characteristics: its irregular blended orange and pink flower coloration, its few small prickles and stipitate glands near the base of the flower receptacle and its very crisp and very glossy foliage. The plant has an upright moderately spreading growing habit, suitable for outdoor garden decoration.

Asexual reproduction of the new variety by budding as performed in Kern County and Upland, Calif., shows that the foregoing and other distinguishing characteristics come true to form and are established and transmitted through succeeding asexual propagations. 'WEKvoosun' may be asexually propagated by budding and grafting. The budding and grafting successfully occurred on the plant/rootstock *Rosa hybrida* cv. 'Dr. Huey'.

Comparison with Parents

The new rose may be distinguished from its seed parent, 'AROmiclea' by the following combination of characteristics: whereas 'WEKvoosun' bears medium to somewhat large sized flowers (about 9.0 to about 12.8 cm. in diameter) of blended orange and pink coloration, 'AROmiclea' bears significantly larger flowers (about 11.5 to about 14.0 cm. in diameter) of chatoyant orange coloration. The new variety bears many pistils (average about 140), whereas the seed parent bears significantly lesser pistils (average about 75).

the new variety may be distinguished from its pollen parent, 'FRYxotic' by the following combination of characteristics: whereas 'WEKvoosun' bears medium to somewhat large sized flowers (about 9.0 to about 12.8 cm. in diameter) of blended orange and pink coloration, 'FRYxotic' bears significantly larger flowers (about 11.0 to about 14.0 cm. in diameter) of pink with an apricot gold center coloration. The new variety bears very glossy foliage, whereas the pollen parent bears semi-glossy foliage.

Comparison with the Closest Commercially Available Cultivar

The closest commercially available cultivar to the new variety is the seed parent 'AROmiclea'.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (1966) except where common terms of color definition are employed.

DESCRIPTION OF THE NEW VARIETY

The following description is of 3 to 4 year-old rose plants of the new variety grown outdoors in Upland, Calif. in the month of November. Phenotypic expression may vary with environmental, cultural and climatic conditions, as well as differences in conditions of light and soil.

Flower:

The new variety usually bears its flowers singly. Flowers are borne on moderately strong short to medium length stems (about 23 to about 50 cm.). Outdoors, the plant blooms abundantly and nearly continuously during the growing season. The flowers have a moderate tea somewhat spicy fragrance.

Bud:

The peduncle is about 2.6 to about 7.0 cm. in length, of average to somewhat heavy caliper (about 0.3 to about 0.5 cm. in diameter), and usually erect to moderately stiff. It is rough, with some stipitate glands and many small prickles. Peduncle color is between 144A and 146B sometimes lightly suffused, especially on the side exposed to the sun, with between 187C and 183B.

Before the calyx breaks, the bud is about 1.2 to about 2.0 cm. in diameter at the widest point, about 1.6 to about 2.5 cm. in length, and ovoid to moderately pointed in shape. The surface of the bud bears few foliaceous appendages, some hairs and many stipitate glands, usually with stout moderately cut foliaceous parts extending beyond the tip of the bud about ¾ or more of its length. Bud color is between 144A and 138A.

The sepals are about 2.7 to about 5.2 cm. in length and about 0.8 to about 1.0 cm. in width at the widest point. The outer surface color of the sepal is between 144A and 138A. The foliaceous appendages are of similar color to the sepals usually moderately suffused with between 183B and 187A. The inner surface color of the sepal is between 138B and 137B and covered with fine wooly tomentum; sepal margins are lined with some stipitate glands and hairs.

The receptacle of the flower is moderately short to average in length (about 0.4 to about 0.7 cm.) and somewhat thin in caliper (about 0.6 to about 1.3 cm. in diameter). The receptacle is moderately rounded to somewhat urn-shaped in form. Its surface is mostly smooth sometimes with few small prickles and stipitate glands near its base. The receptacle has thick fleshy walls. The receptacle color is between 144A and 138A.

As the petals open (after the calyx breaks), the bud is about 1.3 to about 3.4 cm. in diameter at the widest point, about 2.7 to about 3.8 cm. in length, and ovoid in form. The color of the under surfaces of the newly opened petals is between 53A and 46A often suffused with as dark as between 187A and 59A. At the point where the petal attaches, there is a small zone of between 1B and 154C. The color of the upper surfaces of the newly opened petals is between 45A and 46B. At the point where the petal attaches, there is a moderately small zone of between 1A and 2B.

Bloom:

When fully open, the bloom ranges from about 9.0 to about 12.8 cm. in diameter. Petalage is double with about 29 to 41 petals and about 3 to 4 petaloids irregularly arranged. When partially open, the bloom form is moderately high centered, and the petals are somewhat tightly spiraled to moderately cupped with petal edges moderately reflexed outward. When fully open, the bloom form is more cupped, and the petals are loosely cupped to somewhat undulated with petal edges moderately reflexed to almost rolled outward.

Petals:

The substance of the petals is moderately heavy to somewhat slight and of moderately thin to medium thickness, with upper surfaces slightly satiny and under surfaces somewhat shiny to almost matte. The petals are about 3.7 to about 5.8 cm. in length and about 3.1 to about 6.4 cm. in width at the widest point. Petal margins are entire.

The outer petals are nearly round to somewhat obovate in shape with rounded apices.

The inner petals are moderately obovate in shape with rounded apices.

Petaloids are about 1.1 to about 3.7 cm. in length and about 0.9 to about 2.8 cm. in width at the widest point. Petaloids are irregularly shaped somewhat oblanceolate to subulate with rounded apices.

Newly opened flower:

The under surface color of the outer petals is between 46C and 39B gradually suffusing toward the petal edge with between 53D and 55B and often suffused on the lower two thirds of the petal with as dark as between 187A and 61A. At the point where the petal attaches, there is a small zone of between 12A and 13A. The upper surface color of the outer petals is between 43A and 46C gradually suffusing toward the petal edge with between 53D and 55A. At the point where the petal attaches, there is a moderately small zone of between 14A and 15A.

The under surface color of the intermediate petals is between 46C and 39B gradually suffusing toward the petal edge with between 51A and 55B. The upper surface color of the intermediate petals is between 43A and 41B gradually suffusing toward the petal edge with between 50B and 51B.

The under surface color of the inner petals is between 46C and 39B gradually suffusing toward the petal edge with between 46D and 55B. The upper surface color of the inner petals is between 33A and 31B gradually suffusing toward the petal edge with between 43B and 58D.

The under and upper surface color of the petaloids are similar in coloration to the upper and under surfaces of the inner petals.

The general tonality of the newly opened flower is irregular in color to as dark as between 43A and 46C to as light as between 33A and 31B.

Three-day-old flower:

The under surface color of the outer petals is between 58B and 55A and often suffused on the lower two third of the petal with as dark as between 187A and 61A. At the point where the petal attaches, there is a small zone of between 12B and 13B. The upper surface color of the outer petals is between 52A and 43C gradually suffusing toward the petal edge with between 58B and 55A sometimes blushed with between 53B and 53A. At the point where the petal attaches, there is a moderately small zone of between 12A and 13B.

The under surface color of the intermediate petals is between 58B and 55A. The upper surface color of the intermediate petals is between 50A and 43C gradually suffusing toward the petal edge with between 58B and 55A sometimes blushed with between 53B and 53A.

The under surface color of the inner petals is between 53C and 54A. The upper surface color of the inner petals is between 45B and 43C.

The under and upper surface color of the petaloids are similar in coloration to the upper and under surfaces of the inner petals.

The general tonality of the three-day-old flower is irregular in color to as dark as between 45B and 43C to as light as between 52A and 43C.

On the spent bloom, the petals usually drop off cleanly.

In November in Upland, Calif., blooms on the bush growing outdoors generally last about four to five days. Cut roses from plants grown outdoors and kept at normal indoor living temperatures generally last about four to five days.

Male reproductive organs:

Stamens are many in number (average about 185) and are arranged regularly about the pistils; a few are mixed with petaloids. The filaments are of medium to long length (about 0.6 to about 1.6 cm.) most with anthers. Filaments are between 14B and 13A sometimes lightly suffused with between 32A and 33B in color. The anthers are moderately small for the class and all open approximately at the same time. Anther color when immature is near 22A on the external part and near 18B on the internal part. Anther color at maturity is near 164B on the external part and near 200A on the internal part. Pollen is moderately abundant and between 16C and 18A in color.

Female reproductive organs:

Pistils vary in number (average about 140). The styles are somewhat uneven, average to somewhat long in length (about 0.6 to about 0.9 cm.), moderately thin in caliper, and loosely separated to somewhat columnar. Stigma color is between 20A and 21C. Style color is between 4D and 2D sometimes moderately suffused with near 53B. Ovaries are usually all enclosed in the calyx.

Hips have not been observed on this variety when grown in Upland, Calif.

Foliage:

The compound leaves are usually comprised of three to five leaflets and are borne abundantly. The five-leaflet leaves are about 8.8 to about 12.3 cm. in length and about 7.8 to about 9.2 cm. in width at the widest point, very crisp to somewhat leathery in texture, and very glossy in finish. The terminal leaflets are about 4.7 to about 6.2 cm. in length and about 2.7 to about 4.5 cm. in width at the widest point, shaped obovate with acute apices and rounded bases. Their margins are usually simply serrate.

The upper surface color of the mature leaf is between 139A and 137A. The under surface color of the mature leaf is between 147B and 138B. The upper surface color of the young leaf is between 147A and 144A, often heavily suffused with between 187A and 187B. The under surface color of the young leaf is between 147B and 138B, often heavily suffused with between 187B and 183A.

The rachis is moderately light in caliper and rough. The upper side is deeply grooved with some stipitate glands on the edges of the grooves. The under side of the rachis is rough with some stipitate glands and small prickles. The rachis color is near 145A on the under side and near 137C on the upper side, often heavily suffused especially on the young leaf with between 187B and 183A.

The stipules are about 1.0 to about 1.9 cm. in length and moderately wide (about 0.4 to about 0.9 cm.) with medium length straight points that usually turn out at an angle of more than 45 degrees and often recurve toward the stem. The stipules color is between 137B and 146C.

The petiole is moderately light in caliper and rough. The upper side is deeply grooved with some stipitate glands on the edges of the grooves. The under side of the petiole is rough with some stipitate glands and small prickles. The petiole is about 0.6 to about 1.2 cm. in length and about 0.1 to about 0.15 cm in diameter at the widest point. The petiole color is near 145A on the under side and near 137C on the upper side, often heavily suffused especially on the young leaf with between 187B and 183A.

The plant displays an average degree of resistance to powdery mildew and rust as compared to other commercial varieties grown under comparable conditions in Upland, Calif. The plant's winter hardiness and drought/heat tolerance are yet to be determined.

Growth:

The plant has an upright moderately spreading medium to somewhat tall growing habit (about 150 to about 180 cm. in height and about 62 to about 76 cm. spread at the widest point), with full branching. It displays moderately vigorous growth and the canes are of somewhat light to medium size caliper for the class.

The color of the major stems is between 152A and 148A. They bear many large prickles that are about 0.5 to about 0.8 cm. in length. The large prickles are angled slightly downward with a very long broad oval base; prickle color is between 165A and 164A often moderately suffused with near 201C. The major stem bears few small prickles of similar shape and coloration.

The color of the branches is between 146A and 139B. They bear many large prickles which are of similar size to the large prickles on the major stems. The large prickles are angled moderately downward to somewhat hooked with a very long broad oval base; prickle color is between 164A and 165B. The branches bear few small prickles of similar shape and coloration.

The color of the new shoots is between 144A and 146B often heavily suffused with between 187B and 183A. They bear many large prickles which are of similar size and shape to the large prickles on the branches; prickle color is between 151B and 151A often heavily suffused with between 187B and 187C. The shoots bear few small prickles of similar shape and coloration.

I claim:

1. A new and distinct Hybrid Tea rose plant of the variety substantially as described and illustrated herein.

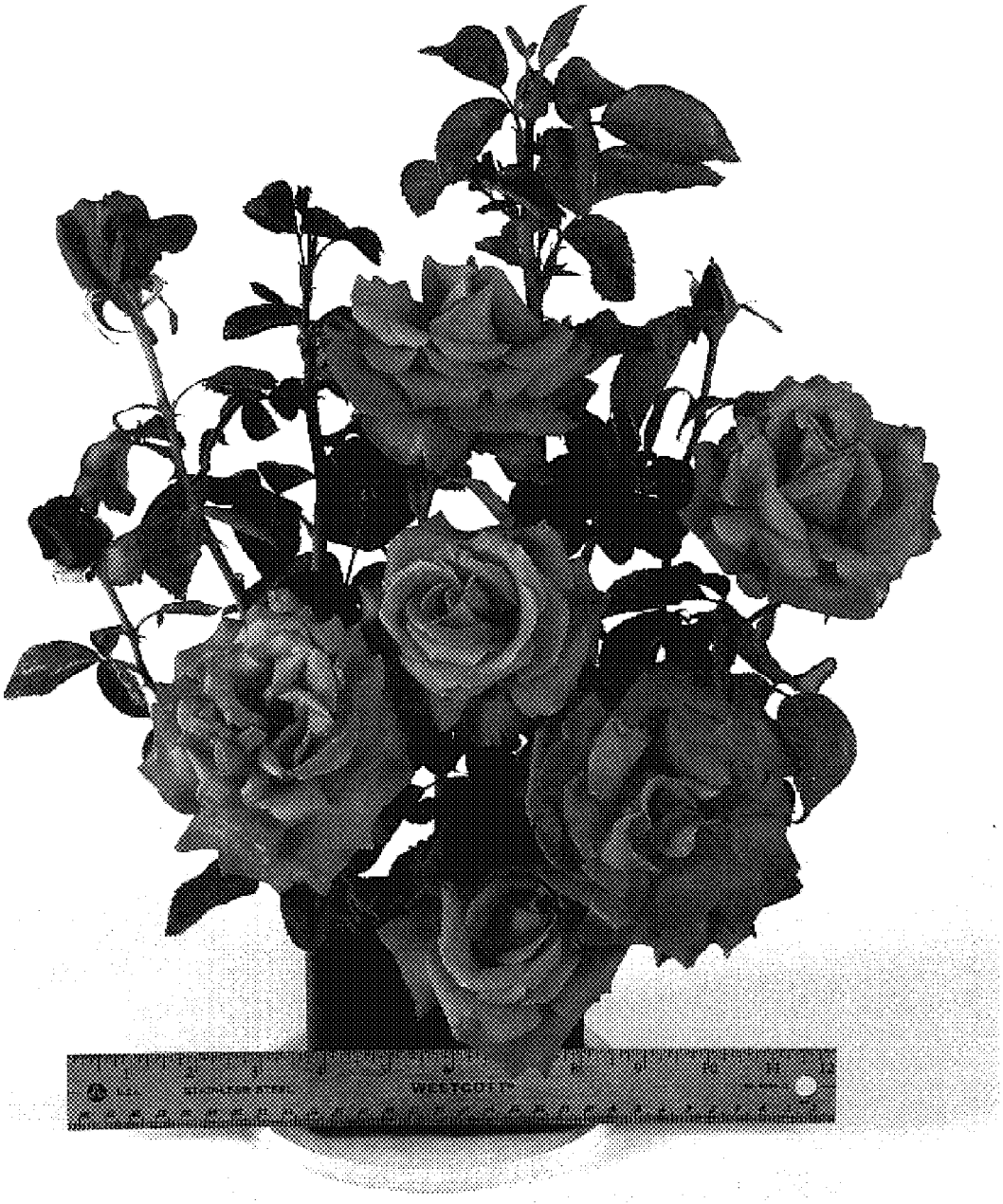

* * * * *